United States Patent [19]

Molteni et al.

[11] Patent Number: 5,008,547
[45] Date of Patent: Apr. 16, 1991

[54] DENTAL X-RAY IMAGE DETECTION SYSTEM

[75] Inventors: Roberto Molteni; Giulio Zanmarchi, both of Monza, Italy

[73] Assignee: U.S. Philips Corporation, New York, N.Y.

[21] Appl. No.: 444,930

[22] Filed: Nov. 30, 1989

[30] Foreign Application Priority Data

Dec. 8, 1988 [EP]  European Pat. Off. ......... 88202809.5

[51] Int. Cl.⁵ .................................................. A61B 6/14
[52] U.S. Cl. ........................................ 250/368; 378/99
[58] Field of Search ................ 250/368; 378/191, 99, 378/114, 40

[56] References Cited

U.S. PATENT DOCUMENTS 4,247,165  1/1981  Versluis ........................... 350/96.27
4,593,400  6/1986  Mouyen ............................... 378/99
4,878,234  10/1989  Pfeiffer et al. ....................... 378/99

FOREIGN PATENT DOCUMENTS 0149502  1/1985  European Pat. Off. .
0279293  2/1988  European Pat. Off. .
0279294  2/1988  European Pat. Off. .
0285214  3/1988  European Pat. Off. .
1439096  10/1968  Fed. Rep. of Germany ...... 250/213 VT Primary Examiner—Carolyn E. Fields
Attorney, Agent, or Firm—William Squire

[57] ABSTRACT

A fibre optics device provided with an obliquely cut end surface transmits an optical image projected onto that surface to a second end face thereof forming on the second end face on image with a reduced surface area. Using a crossed cascade of two fibre optics devices, an image area is reduced in two directions.

18 Claims, 1 Drawing Sheet

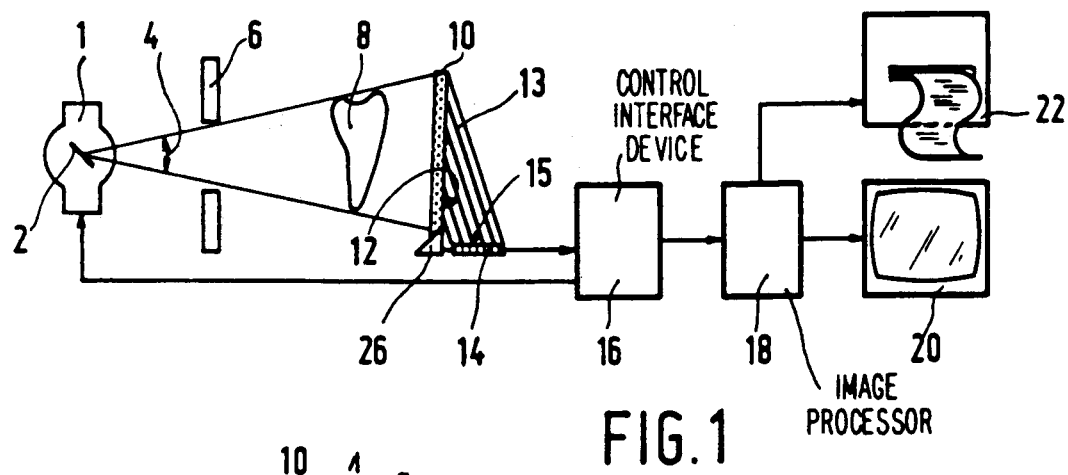
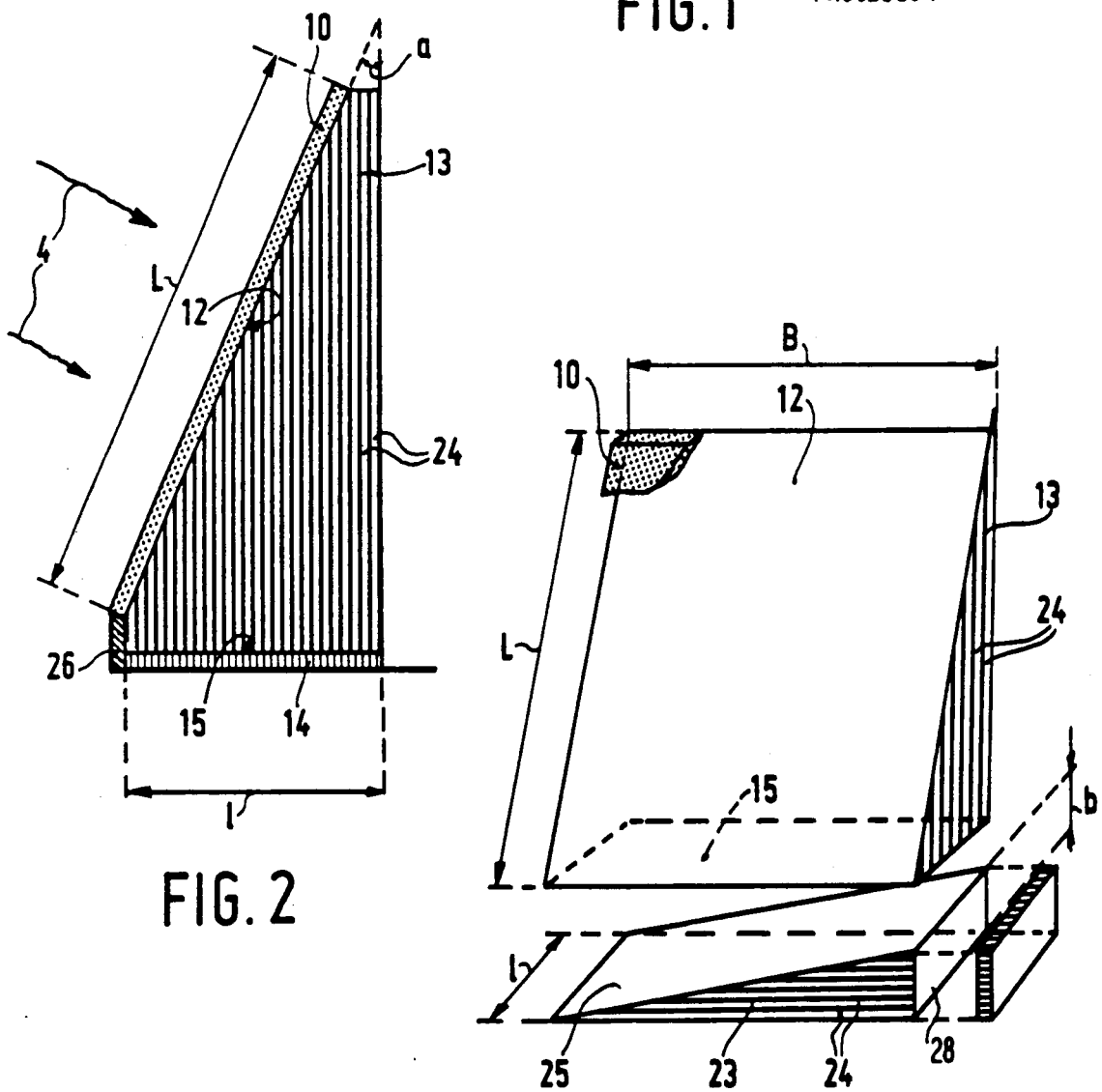
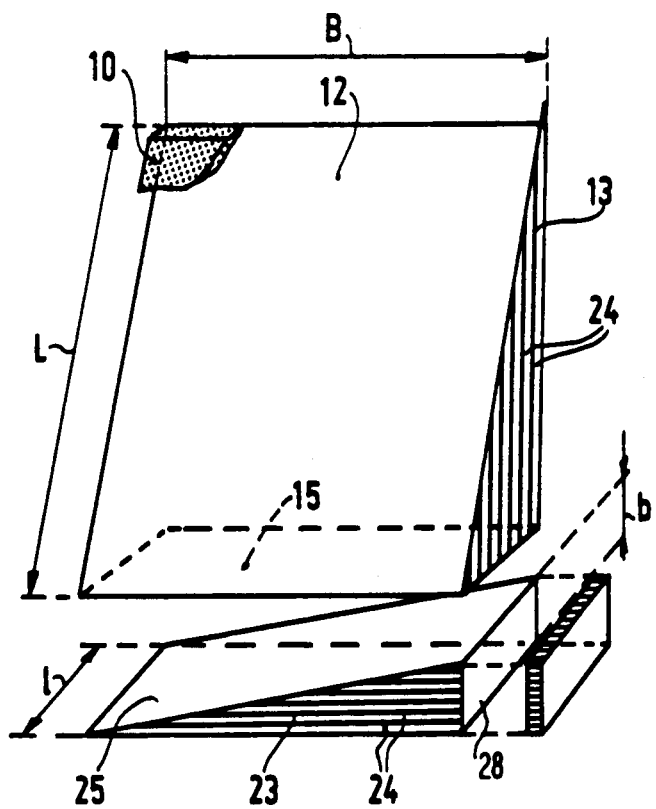

DENTAL X-RAY IMAGE DETECTION SYSTEM

The invention relates to a dental X-ray image detection system provided with an optical sensitive sensor being fibre optically coupled to a luminescent screen.

Such a detection system is known from U.S. Pat. No. 4,593,400. In this system a luminescent screen is optically coupled to a CCD matrix as optical sensor with the aid of a tapered fibre optical device such that the surface area of an X-ray image projected on the luminescent layer is reduced to a smaller surface area to be projected on the CCD matrix.

For a practical device the reduction in the dimension of the X-ray image and the sensor image should be relatively high in order to have an X-ray image large enough to encompass at least a full tooth and to have the opportunity to make use of a relatively low cost CCD device. The device disclosed in U.S. Pat. No. 4,593,400 is not suited to realise such a high image reduction at acceptable costs without the risk that the image will become deteriorated in the fibre optics device due to irregularities therein as a consequence of the too strong tapering or that the fibre optics device becomes unacceptable long for practical use. A further disadvantage of the known apparatus is that the CCD matrix must be protected against direct X-ray radiation from the source as well as against X-rays scattered in the object to be examined or in parts of the apparatus. In the known apparatus the detecting device including the CCD matrix is located in direct view of the X-ray source. X-ray protection has to be added between the luminescent layer and the sensor. Such a protection can easily have an adverse effect on the image forming.

In the known apparatus the screening is executed by incorporating X-ray absorbing material in the optical transmitting fibres for preventing passage of X-rays by the luminescent layer. Such material has a negative effect on the image transmission, especially fue to the direct view orientation. Also the core glass must be X-ray absorbing with all its negative effects on the light transmission.

From EP 149 502 a fibre optically coupled X-ray detection system is known but there the need to have a small dimension in the direction of the imaging X-ray beam does not exist. The same can be said of the scanning apparatus disclosed in EP 279 293.

It is a main object to alleviate the mentioned disadvantages in a detecting system for a dental X-ray apparatus as defined above. A detection system according to the present invention comprises a fibre optical device having a first surface obliquely cut with respect to the fibres, introducing a surface area reduction between this surface and a second surface of the device optically connected thereto.

In a further embodiment the fibre optics device reduces the long axis of a rectangular X-ray image with about a factor 3 adapting the optical image area to a sensor surface area having a long axis substantial equal to the short axis of the X-ray image and a small axis substantial equal to a third of the long X-ray image area axis. Using two fibre optics elements in cascade each introducing a linear reduction of roughly a factor 3, a reduction of an X-ray image of about $18 \times 24$ mm$^2$ can be reduced to a CCD matrix sensor area of $6 \times 8$ mm$^2$.

In a further embodiment a luminescent layer, preferably of CsI (T1) or Gd2O2S (Tb), is directly coupled to a first obliguely cut surface of the fibre optics device and an optical sensitive sensor preferably a CCD matrix sensor is coupled to a second surface of the fibre optical device optically coupled to the first surface.

In a further embodiment the fibre optics device is cut along two optically coupled surfaces such that substantially a 90° angle is realised between the two surfaces.

In a further embodiment the cladding glass and/or the extra absorbent elements of the fibre optics device contain X-ray absorbing material or are made of lead glass for protecting the sensor from scattered X-rays.

Some embodiments according to the invention will be described more detailed hereinafter with reference to the drawing in which:

FIG. 1 shows schematically a dental X-ray apparatus provided with a detection system according to the invention, and FIGS. 2 and 3 shows examples of fibre optical devices applicable therefore.

A dental X-ray apparatus as shown in FIG. 1 comprises an X-ray source 1 with an anode 2 to generate an X-ray beam 4, which is limited with a diaphragm 6 to irradiate an object 8, here a tooth, to be examined. A shadow image of the object is projected on a luminescent layer 10 converting the X-ray quanta into light quanta. The luminescent layer 10 comprising for example CsI (Tl activated) or Gd2O2S (Tb activated) is directly deposited on a fibre optics surface 12 by vaper deposition, spraying or any other applicable deposition method. Part of the luminescent light generated in the luminescent layer 10 is projected into the fibres of a fibre optics device 13 such that a light optical image, corresponding to the X-ray image projected on the luminescent layer 10 is transmitted by the fibre optics element to an optical sensitive sensor 14 in front of a second surface 15 of the fibre optical device 13. Preferably the sensor 14 is coupled as directly as possible to the fibre optics device 13 in order to avoid loss of imaging light. The optical sensitive sensor 14 preferably is shaped as an electronic matrix sensor in order to enable digital electronics reading and may be constructed as a CCD matrix sensor available on the market. Known CCD matrix sensors have, for example, a detecting surface area of 4.5 times 6.0 mm containing a matrix of about 600 times about 500 elements each measuring about 10 times 10 $\mu$m or a detecting area of about 13 times 9 mm composed of about 575 times 380 elements each measuring about 25 times 25 $\mu$m. The optical sensor 14 is electrically coupled to a signal reading—and signal control interface device 16 to which an image processor 18 is coupled. The control device 16 may provide automatic activation upon X-ray capture by sensor 14. The image processor, in addition to the normal image processing known to be performed in this kind of apparatus such as contrast alteration, edge enhancement, pattern recognition etc., also provides the spatial stretching in one direction which may be necessary to reconstruct the actual geometrical proportions of the image. To the image processor is a coupled 18 monitor 20 for displaying the image of the object or an image derived after image processing and a hard copy unit 22 to produce if asked for a copy on paper or in the alternative, a transparent film or a magnetically or optically registered hard copy of an image.

FIG. 2 shows a fibre optics device 13 more detailed together with a luminescent layer 10 which is for example 50–200 $\mu$m thick and deposited directly on an entrance surface 12 of the fibre optics device. An optical sensitive sensor 14 is directly coupled to an output surface 15 of the fibre optics device. The angle a of surface 12 may be such that an input length L of an X-ray image projected on the luminescent layer 10 is reduced to an output length 1 of the optical image projected on the sensor 14 by fibres 24. The reduction factor may be about 3 and, for a practical device, L can be about 12 mm reduced to 4 mm for the sensor length 1. In the other direction normal to the drawing surface as well to as the X-ray image plane of surface, sensor 14 may measure about 5 to 10 mm. In order to avoid any direct view of the sensor 14 by the X-ray beam 4 an additional screening 26 can be added which also protects against unwanted light impinging on the sensor 14.

FIG. 3 shows an exploded view a cascade of two fibre optics devices 13 and 23. An X-ray image projected on a luminescent screen 10 covering the surface 12 of fibre optics device 13 is projected on a second face 15 of the device reducing the distance L distance 1. An entrance face 25 of the second fibre optics device 23 is preferably directly coupled to the face 15 of device 13. For a good optical transmission at least one of the faces 15 or 25 is roughened such as described in U.S. Pat. No. 4,247,165. The image projected on face 15 is accepted in fibre optics device 23 and transmitted to an exit face 28 thereof reducing distance B of the first optical image corresponding with the X-ray image into distance b to which a dimension of the optical sensor 14 is adapted. That is the reduction is adapted to the relevant distance of sensor 14 which is fixed to the output face 28 of fibre optic elements 23.

In the examples described the fibre optics device is used to reduce the image dimensions. It may be obvious of course due to optical reversibility to use an optical device according to the invention to enlarge the image dimensions. Both actions can also be used without a luminescent layer thus acting only on light optical images. The detection system includes an electrical or electronic circuit as part of device 16 responsive to the received signal produced by sensor 14 to detect the start of X-ray irradiation captive for automatically starting the read-out of the image matrix.

We claim:

1. A dental X-ray detection system for detecting at least one tooth at a time, said system including an optically sensitive sensor optically coupled to a luminescent screen, an optical fibre device for coupling said screen to said sensor comprising in combination with said screen and sensor:
at least one optical fibre having an optical axis, said at least one fibre having first and second end surfaces, one end having a first surface oblique with respect to said optical axis, said first surface defining a first area of a given magnitude, one of said end surfaces comprising means for receiving an X-ray image transmitted thereto by said luminescent screen, said second end surface defining a second area of a second magnitude different than the first area magnitude, the other of said surfaces comprising means for transmitting said received image to said sensor, said device further comprising a cascade of two optically coupled fibre optics devices each comprising means for reducing a dimension of the received X-ray image independently of each other.

2. A dental X-ray detection system as claimed in claim 1 wherein said luminescent screen receives a rectangular X-ray image having long and short dimensions, said sensor having rectangular long and short dimensions, the optical fibre device being arranged for reducing the long dimension of the rectangular X-ray image to the short dimension of the rectangular optical sensor.

3. A dental X-ray detection system as claimed in claim 2 characterized in that the optical sensitive sensor comprises a matrix of CCD sensors.

4. A dental X-ray detection system as claimed in claim 2 characterized in that the luminescent screen is directly deposited on a relevant end surface of one of the fibre optics devices.

5. A dental X-ray detection system as claimed in claim 2 further including display means and a control unit responsive to the transmitted sensed image for automatically activating the display means on X-ray capture.

6. A dental X-ray detection system as claimed in claim 1, wherein the at least one of the fibre optics devices reduces a dimension of the X-ray image by a factor of above three.

7. A dental X-ray detection system as claimed in claim 6 characterized in that the optical sensitive sensor comprises a matrix of CCD sensors.

8. A dental X-ray detection system as claimed in claim 6 characterized in that the luminescent screen is directly deposited on a relevant end surface of one of the fibre optics devices.

9. A dental X-ray detection system as claimed in claim 6 further including display means and a control unit responsive to the transmitted sensed image for automatically activating the display means on X-ray capture.

10. A dental X-ray detection system as claimed in claim 1 wherein the optical sensitive sensor comprises a matrix of CCD sensors.

11. A dental X-ray detection system as claimed in claim 10 further including display means and a control unit responsive to the transmitted sensed image for automatically activating the display means on X-ray capture.

12. A dental X-ray detection system as claimed in claim 1 wherein the luminescent screen is directly deposited on a relevant end surface of one of fibre optics devices.

13. A dental X-ray detection system as claimed in claim 12 further including display means and a control unit responsive to the transmitted sensed image for automatically activating the display means on X-ray capture.

14. A dental X-ray detection system as claimed in claim 1 further including a control unit responsive to the transmitted sensed image for automatically activating the detection system on X-ray capture.

15. A dental X-ray detection system as claimed in claim 1 wherein in the optical fibre device includes X-ray absorbing material.

16. A dental X-ray detection system as claimed in claim 1 wherein the optical fibre device includes lead.

17. A dental X-ray detection system as claimed in claim 11 wherein the second surface of the at least one optical fibre is oblique with respect to the optical axis of the at least one fibre.

18. A dental system as claimed in claim 1 wherein said cascaded devices are cascaded to cumulatively reduce said dimension.